United States Patent
Zimmer (10) Patent No.: US 11,220,668 B2
(45) Date of Patent: Jan. 11, 2022

(54) METHOD FOR REDUCING THE TRISULFIDE LEVEL IN PROTEINS

(71) Applicant: Merck Patent GmbH, Darmstadt (DE)

(72) Inventor: Aline Zimmer, Gross-Gerau (DE)

(73) Assignee: Merck Patent GmbH, Darmstadt (DE)

( * ) Notice: Subject to any disclaimer, the term of this patent is extended or adjusted under 35 U.S.C. 154(b) by 410 days.

(21) Appl. No.: 16/096,805

(22) PCT Filed: Apr. 25, 2017

(86) PCT No.: PCT/EP2017/059691
§ 371 (c)(1),
(2) Date: Oct. 26, 2018

(87) PCT Pub. No.: WO2017/186654
PCT Pub. Date: Nov. 2, 2017

(65) Prior Publication Data
US 2020/0255796 A1 Aug. 13, 2020

(30) Foreign Application Priority Data

Apr. 28, 2016 (EP) .................... 16167461

(51) Int. Cl.
  *C12N 5/00* (2006.01)
  *C07K 1/113* (2006.01)
  *C12P 21/00* (2006.01)
(52) U.S. Cl.
  CPC .......... *C12N 5/0018* (2013.01); *C07K 1/1133* (2013.01); *C12P 21/00* (2013.01); *C12N 2500/32* (2013.01)
(58) Field of Classification Search
  CPC .................................................. C12N 5/0018
  See application file for complete search history.

(56) References Cited

U.S. PATENT DOCUMENTS

| 9,005,926 B2 | 4/2015 | Evans et al. |
| 9,790,533 B2 | 10/2017 | Kshirsagar et al. |
| 10,030,225 B2 | 7/2018 | Von Hagen et al. |
| 2014/0295495 A1 | 10/2014 | Kshirasager |

FOREIGN PATENT DOCUMENTS

| WO | 2011041721 A1 | 4/2011 |
| WO | 2012128551 A1 | 11/2012 |
| WO | 2014075807 A1 | 5/2014 |

OTHER PUBLICATIONS

Hecklau et al., J of Biotechnology, 2016, 218:53-63.*
International Search Report PCT/EP2017/059691 dated Aug. 23, 2018 (pp. 1-3).
Rashmi Kshirsagar et al: "Article Controlling Trisulfide Modification in Recombinant Monoclonal Antibody Produced in Fed-Batch Cell Culture", Biotechnology and Bioengineering, vol. 109, No. 10, Oct. 2012 (Oct. 1, 2012), pp. 2523-2532.
Pristatsky Pavlo et al: "Evidence for trisulfide bonds in a recombinant variant of a human IgG2 monoclonal antibody", Analytical Chemistry, American Chemical Society, US, vol. 81, No. 15, Aug. 1, 2009 (Aug. 1, 2009), pp. 6148-6155.
J.S. Church; D.J. Evans, Spectrochimica Acta Part A, vol. 69, 2008, pp. 256-262.
I.H.Segel; M.J.Johnson, Analytical Biochemistry, vol. 5, 1963, pp. 330-337.
Hecklau et al.; "S-Sulfocysteine simplifies fed-batch processes and increases the CHO specific productivity via anti-oxidant activity", Journal of Biotechnology, 2016, 218, 53-63; doi: dx.doi.org/10.1016/j.jbiotec.2015.11.022 (Date of Publication: Dec. 2, 2015).
Gu: "Characterization of trisulfide modification in antibodies" Analytical Biochemistry 400 (Jan. 18, 2010) 89-98.
Third Party Observation for application No. EP20170718556 dated Oct. 29, 2021 (pp. 1-5).
Communication in application No. EP20170718556 dated Oct. 29, 2021 (pp. 1-93).

* cited by examiner

*Primary Examiner* — Bin Shen
(74) *Attorney, Agent, or Firm* — Millen White Zelano & Branigan, PC; Brion P. Heaney (57) ABSTRACT

The present invention relates to the use of sulfocysteine and derivatives thereof as cell culture additives to reduce the trisulfide levels in proteins produced in cell culture.

20 Claims, 6 Drawing Sheets

METHOD FOR REDUCING THE TRISULFIDE LEVEL IN PROTEINS

The present invention relates to the use of sulfocysteine and derivatives thereof as cell culture additives to reduce the trisulfide levels in proteins like IgGs produced in cell culture.

Recombinant proteins, and in particular, monoclonal antibodies (mAbs), have become an important class of therapeutic compounds employed for the treatment of a broad range of diseases.

Efficient and economic large scale production of such biomolecules, e.g., therapeutic proteins including antibodies is an increasingly important consideration for the biotechnology and pharmaceutical industries. Typically, proteins are produced using cell culture methods, e.g. using either mammalian or bacterial cell lines recombinantly engineered to produce the protein of interest.

However, such recombinantly produced proteins show considerable heterogeneity. Such heterogeneity can result from chemically-induced modifications such as oxidation, deamidation, and glycation as well posttranslational modifications such as proteolytic maturation, protein folding, glycosylation, phosphorylation, and disulfide bond formation. Molecular heterogeneity is undesirable especially if the therapeutic proteins are meant for use in humans and have to be approved by regulatory agencies, such as the Food and Drug Administration (FDA).

One molecular heterogeneity that has gained particular interest is the formation of trisulfide bonds.

Antibodies (or immunoglobulins) are composed of four polypeptide chains: two light chain polypeptides (LC) and two heavy chain polypeptides (HC). The four chains are typically joined in a "Y" configuration by disulfide bonds that form between cysteine residues present in the heavy and light chains. These disulfide linkages govern the overall structure of the native HC2LC2 tetramer. Typically, antibodies contain four interchain disulfide bonds, including two hinge region disulfides that link the H chains, and one disulfide bond between each heavy H and L chain. In addition, twelve intrachain disulfide linkages may involve each remaining cysteine residue present in the molecule. Incomplete disulfide bond formation, or bond breakage via oxidation or beta-elimination followed by disulfide scrambling, are all potential sources of antibody heterogeneity. In addition, a further type of modification, namely trisulfide ($-CH_2-S-S-S-CH_2-$) bond formation, was recently reported. Further information on trisulfide bond formation can be found in Pristatsky et al., Anal. Chem. 81: 6148 (2009).

Rashmi Kshirsagar et al., Biotechnology and Bioengineering, Vol. 109, No. 10, October, 2012, page 2523-2532 suggest amending and especially reducing the cysteine content in cell culture media as they see a relation between the cysteine content and the formation of trisulfide bonds.

WO 2011 041721 discloses a method for converting trisulfide bonds to disulfide bonds in proteins by allowing the proteins in a solution to contact and associate with a solid support and by then exposing said proteins to a solution comprising a reducing agent.

WO2012158551 discloses a method for reducing the formation of trisulfide bonds in proteins during large scale production comprising culturing cells expressing said proteins in the presence of an effective amount of an inhibitor of cysteine degradation, e.g. glutathione, pyruvate etc.

It would be favorable to find other, less complicated and/or more efficient ways to reduce the trisulfide level in proteins.

It has been found that if cysteine in the cell culture medium is replaced by S-sulfocysteine and/or salts thereof, the amount of trisulfide bonds in the proteins produced in said cell culture medium is decreased compared to the same cell culture medium comprising cysteine.

This invention is consequently directed to a method for reducing the formation of trisulfide bonds in proteins comprising culturing cells expressing said proteins whereby a feed medium is added to the cell culture one or more times during cell culture that does not contain any significant amount of cysteine or cystine but comprises S-sulfocysteine and/or salts thereof, whereby trisulfide linkage formation in said proteins is reduced relative to cells cultured in a cell culture medium where cysteine and/or cystine in the feed medium has not been partially or preferably fully replaced by S-sulfocysteine and/or salts thereof.

In a preferred embodiment, the S-sulfocysteine and/or salts thereof is S-sulfocysteine sodium salt.

In a preferred embodiment, the pH of the feed comprising S-sulfocysteine and/or its salts is between 6.8 and 7.5.

In another preferred embodiment, S-sulfocysteine and/or a S-sulfocysteine salt are added in an amount so that their concentration in the cell culture is between 0.4 and 50 mM.

In one embodiment, the cells are cultured in a cell culture medium comprising at least one or more saccharide components, one or more amino acids, one or more vitamins or vitamin precursors, one or more salts, one or more buffer components, one or more co-factors and one or more nucleic acid components.

In one embodiment, trisulfide linkage formation between the light chain and the heavy chain in said proteins is reduced relative to cells cultured in a cell culture medium where cysteine and/or cystine in the feed medium has not been replaced by S-sulfocysteine and/or salts thereof.

In one embodiment, the method of the invention is performed by

Filling into a bioreactor cells and a liquid cell culture medium

Incubating the cells in the bioreactor

Continuously over the whole time of the incubation of the cells in the bioreactor or once or several times within said incubation time adding a cell culture medium, which is in this case a feed medium, to the bioreactor whereby the feed medium comprises S-sulfocysteine and/or salts thereof and no significant amount of cysteine and/or cystine. It is of course possible to also add other feed media which do not comprise S-sulfocysteine and/or salts thereof. Preferably, no feed media are added which contain cysteine and/or cystine.

Preferably the feed medium comprises S-sulfocysteine and/or a S-sulfocysteine salt in a concentration between 1 and 100 mmol/l, preferably between 5 and 20 mmol/l.

Preferably, over the whole time of the incubation of the cells in the bioreactor no feed medium is added which contains cysteine and/or cystine.

"Trisulfide bonds" are generated by the insertion of an additional sulfur atom into a disulfide bond, thereby resulting in the covalent bonding of three consecutive sulfur atoms. Trisulfides are a posttranslational modification. Trisulfide bonds can form between cysteine residues in proteins and can form intramolecularly (i.e., between two cysteines in the same protein) or intermolecularly (i.e. between two cysteines in separate proteins). Trisulfides were e.g. detected in interchain linkages, predominantly in the light-heavy linkages.

Figure 1:
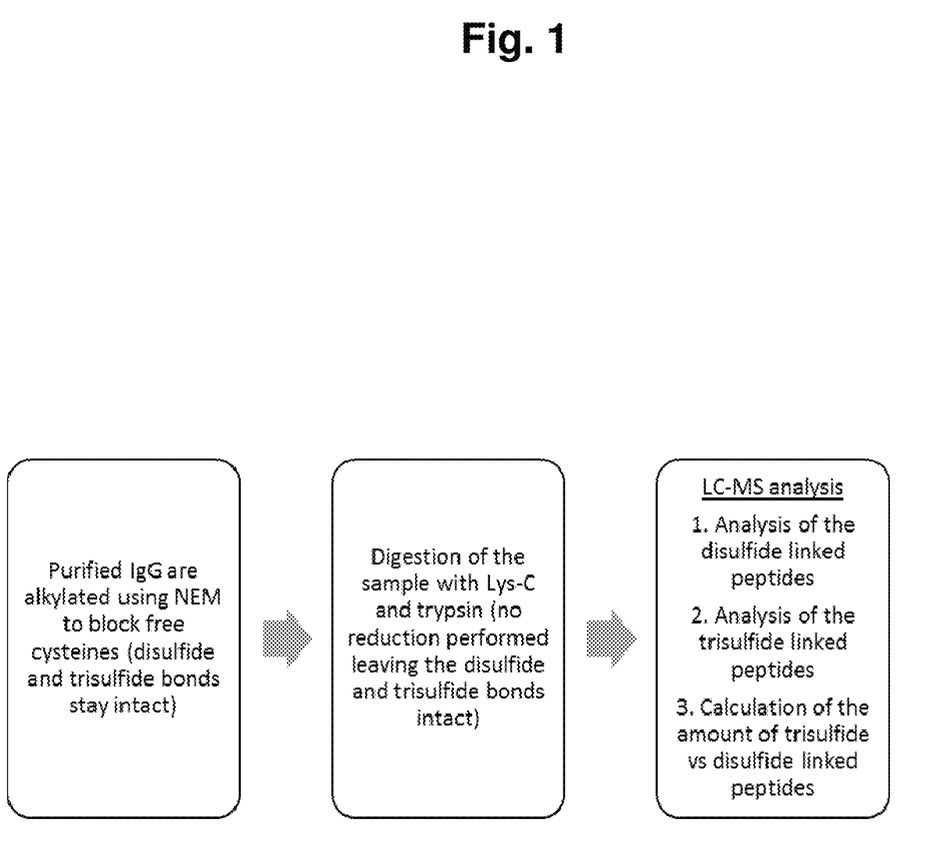
FIG. 1 shows Strategy used to monitor trisulfide levels in IgG. Further details can be found in the examples.
Figure 2:
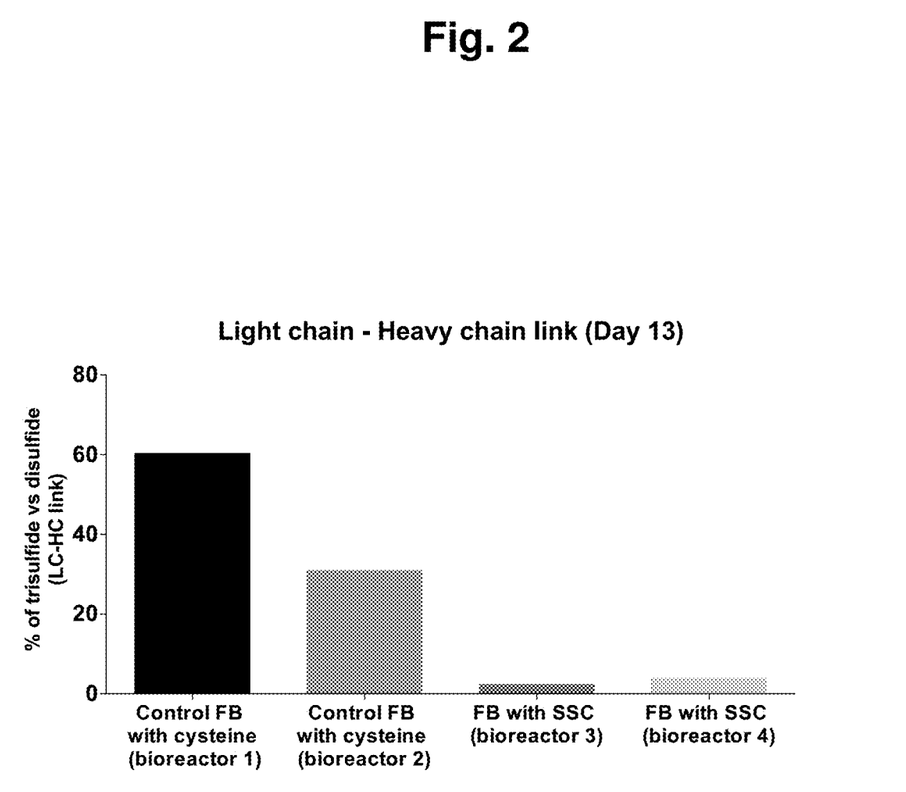
FIGS. 2-5 show the relative quantification of trisulfide linked peptides in the combined Lys-C/tryptic digest at day 13 and day 18 of the FB process. Further details can be found in the examples.
Figure 3:
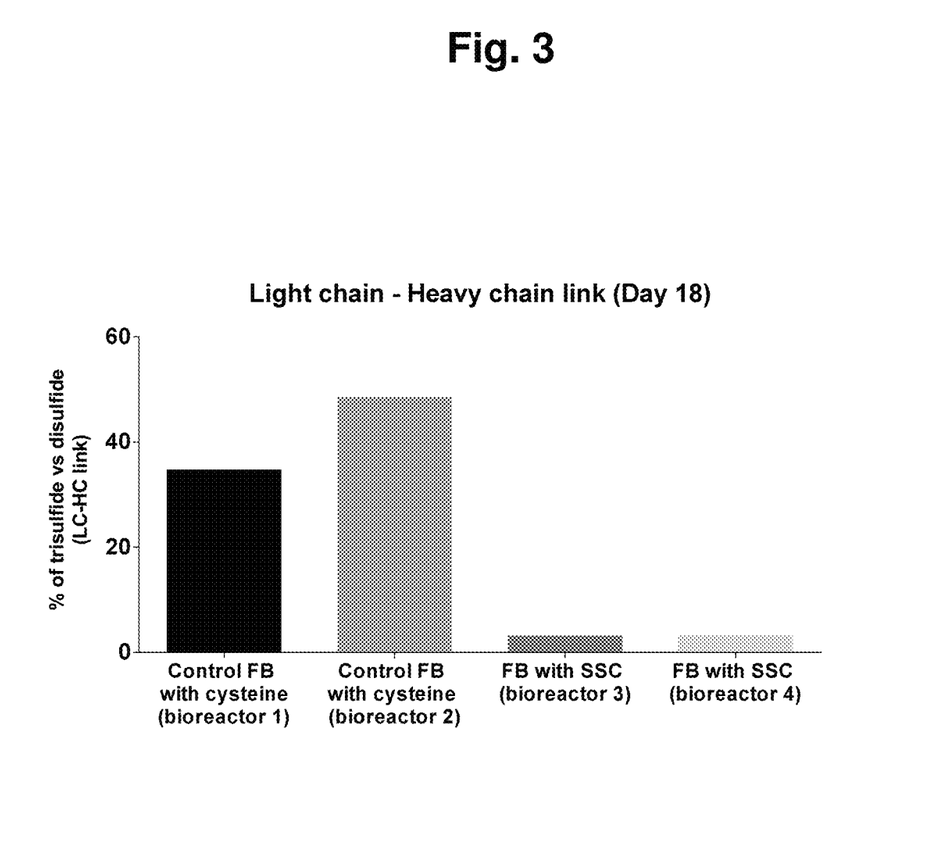
Figure 4:
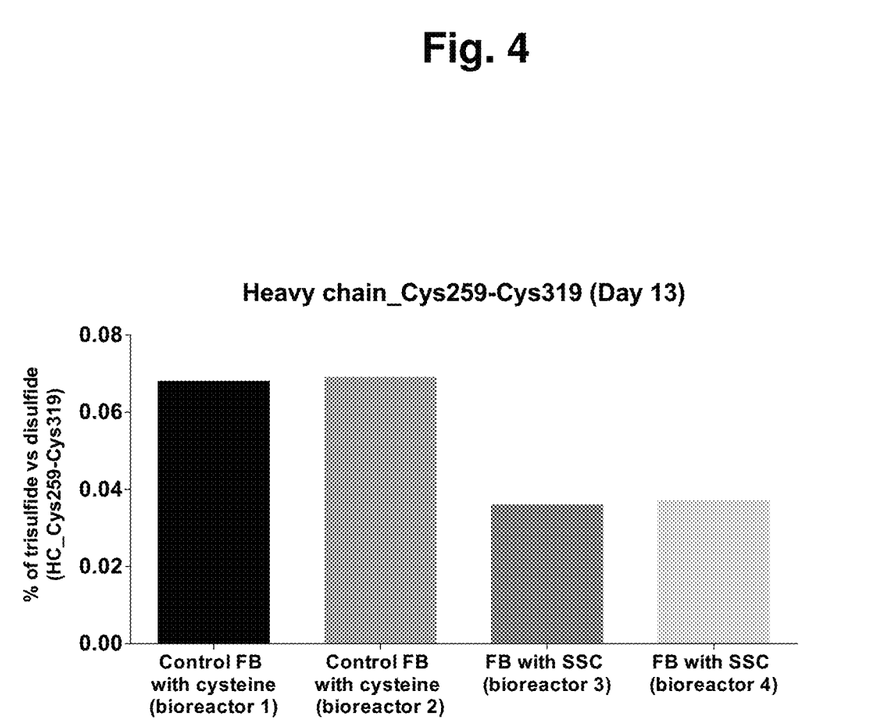
Figure 5:
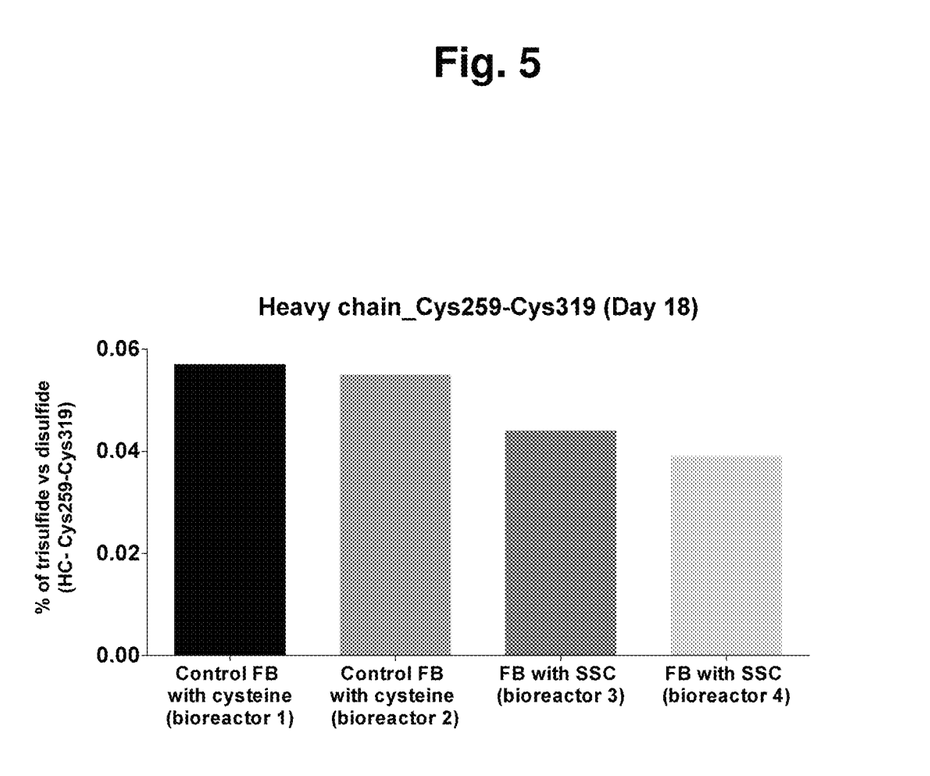

The presence of trisulfide bonds can be detected using e.g. peptide mapping and can be detected based on an increase in mass of the intact protein due to an extra sulfur atom (32 Da). Trisulfide bonds can thus be detected using mass spectrometry, or by high pressure liquid chromatography and mass spectrometry (peptide mapping utilizing a LC-MS system). FIG. 1 shows a general scheme of how such an analysis can be performed. Further details can be found in the examples.

"Proteins" are macromolecules consisting of one or more chains of amino acid residues. Oligopeptides and preferably polypeptides are included within the definition of protein. Proteins perform a vast array of functions within living organisms, including catalyzing metabolic reactions, DNA replication, responding to stimuli, and transporting molecules from one location to another. Proteins differ from one another primarily in their sequence of amino acids. Most proteins fold into unique 3-dimensional structures. Proteins can be e.g. naturally occurring proteins or, preferably, recombinantly produced proteins. Examples of proteins are enzymes or preferably antibodies. Also included as proteins according to the present invention are fragments, derivatives, analogs, or variants of the foregoing proteins, and any combination thereof.

The term "antibody" refers to a protein which has the ability to specifically bind to an antigen. Typically, antibodies are having a basic four-polypeptide chain structure consisting of two heavy and two light chains, said chains being stabilized, for example, by interchain disulfide bonds. Antibodies may be monoclonal or polyclonal and may exist in monomeric or polymeric form, for example, IgM antibodies which exist in pentameric form and/or IgA antibodies which exist in monomeric, dimeric or multimeric form. Antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins. According to the present invention fusion proteins are also encompassed by the term "antibody".

S-sulfocysteine, also called (S)-2-amino-3-sulfosulfanyl-propanoic acid is a product e.g. obtainable by the condensation of sulfuric acid and cysteine. Suitable salts are alkaline metal or alkaline earth metal salts, e.g. the lithium salts, the sodium salts, the potassium salts, the calcium salts or the magnesium salts or mixtures thereof. Preferred are sodium salts, the potassium salts, the calcium salt and the magnesium salt, most preferred are the sodium salts, especially the sodium salt.

S-sulfocysteine and its salts can also be shown by the following formula I:

with R being and X being H, Li, Na, K, ½ Ca, ½ Mg, preferably H, Na, K. The term propanoic acid can also be used instead of the term propionic acid.

The synthesis of 2-Amino-3-sulfosulfanyl-propanoic acid, also called (S)-2-Amino-3-sulfosulfanyl-propanoic acid, S-sulfo-cysteine or cysteine-S-sulfate, and its salts is disclosed for example in I. H. Segel and M. J. Johnson, Analytical Biochemistry 5 (1963), 330-337 and J. S. Church, D. J. Evans, Spectrochimica Acta Part A 69 (2008) 256-262. S-sulfo-cysteine is commercially available from Sigma-Aldrich, US. The sodium salt is further commercially available from Bachem, Switzerland.

A cell culture is any setup in which cells are cultured. A cell culture is for example used to produce target molecules like pharmaceuticals, especially recombinant proteins like antibodies.

A cell culture medium is any mixture of components which maintains and/or supports the in vitro growth of cells. It might be a complex medium or a chemically defined medium. The cell culture medium can comprise all components necessary to maintain and/or support the in vitro growth of cells or only some components so that further components are added separately. Examples of cell culture media are full media which comprise all components necessary to maintain and/or support the in vitro growth of cells as well as media supplements or feeds. A full medium also called base medium typically has a pH between 6.8 and 7.8. A feed medium preferably has a pH below 8.5. The cell culture media that are used according to the present invention are preferably chemically defined cell culture media.

Typically, the cell culture media according to the invention are used to maintain and/or support the growth of cells in a bioreactor and to support the IgG production of said cells.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. They are manufactured for the purpose of dissolving in water and/or aqueous solutions and in the dissolved state are designed, often with other supplements, for supplying cells with a substantial nutrient base for growth and/or production of biopharmaceuticals from said cells.

Most biopharmaceutical production platforms are based on fed-batch cell culture protocols. The aim typically is to develop high-titer cell culture processes to meet increasing market demands and reduce manufacturing costs. Beside the use of high-performing recombinant cell lines, improvements in cell culture media and process parameters are required to realize the maximum production potentials In a fed-batch process, a base medium supports initial growth and production, and a feed medium prevents depletion of nutrients and sustains the production phase. The media are chosen to accommodate the distinct metabolic requirements during different production phases. Process parameter settings—including feeding strategy and control parameters—define the chemical and physical environments suitable for cell growth and protein production.

A feed or feed medium is a cell culture medium which is not the basal medium that supports initial growth and production in a cell culture but the medium which is added at a later stage to prevent depletion of nutrients and sustains the production phase. A feed medium can have higher concentrations of some components compared to a basal culture medium. For example, some components, such as, for example, nutrients including amino acids or carbohydrates, may be present in the feed medium at about 5×, 6×, 7×, 8×, 9×, 10×, 12×, 14×, 16×, 20×, 30×, 50×, 100×, 200×, 400×, 600×, 800×, or even about 1000× of the concentrations in a basal medium.

According to the present invention a feed medium that does not contain any significant amounts of cysteine and/or cystine but S-sulfocysteine and/or its salts as a replacement is any medium that contains cysteine and/or cystine in an amount of less than 5% (w/w) preferably less than 1% (w/w) of the amount of S-sulfocysteine and/or its salts, most preferred it contains no cysteine and/or cystine but only comprises S-sulfocysteine and/or its salts as well as potential other feed components other than cysteine and/or cystine.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts, hydrolysates or digests or other chemically poorly defined components. Chemically undefined or poorly defined chemical components are those whose chemical composition and structure is not known, are present in varying composition or could only be defined with enormous experimental effort—comparable to the evaluation of the chemical composition and structure of a protein like albumin or casein.

A powdered cell culture medium or a dry powder medium is a cell culture medium typically resulting from a milling process or a lyophilisation process. That means the powdered cell culture medium is a granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated. A powdered cell culture medium can also be a granulated cell culture medium, e.g. dry granulated by roller compaction.

Powdered cell culture media are preferably produced by mixing all components and milling them. The mixing of the components is known to a person skilled in the art of producing dry powdered cell culture media by milling. Preferably, all components are thoroughly mixed so that all parts of the mixture have nearly the same composition. The higher the uniformity of the composition, the better the quality of the resulting medium with respect to homogenous cell growth.

The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills.

For use of the milled powdered media a solvent, preferably water (most particularly distilled and/or deionized water or purified water or water for injection) or an aqueous buffer is added to the media and the components are mixed until the medium is totally dissolved in the solvent.

The solvent may also comprise saline, soluble acid or base ions providing a suitable pH range (typically in the range between pH 1.0 and pH 10.0), stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

Cells to be treated with the method according to the present invention may be normal cells, immortalized cells, diseased cells, transformed cells, mutant cells, somatic cells, germ cells, stem cells, precursor cells or embryonic cells, any of which may be established or transformed cell lines or obtained from natural sources. Preferably, the cells are mammalian cells, more preferred BHK, VERO, HEK or CHO cells, most preferred are CHO-S, CHO dhfr- (DG44 and Duxb11), CHO-M and CHOK1 cells.

Cell culture media, especially the full media, typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, fatty acids and/or fatty acid derivatives and/or pluronic acid and/or surface active components like chemically prepared non-ionic surfactants. One example of a suitable non-ionic surfactant are difunctional block copolymer surfactants terminating in primary hydroxyl groups also called poloxamers, e.g. available under the trade name Pluronic® from BASF, Germany.

Saccharide components are all mono- or di-saccharides, like glucose, galactose, ribose or fructose (examples of monosaccharides) or sucrose, lactose or maltose (examples of disaccharides).

Examples of amino acids according to the invention are tyrosine, the proteinogenic amino acids, especially the essential amino acids, leucine, isoleucine, lysine, methionine, phenylalanine, threonine, tryptophane and valine, as well as the non-proteinogenic amino acids like D-amino acids.

Tyrosine means L- or D-tyrosine, preferably L-tyrosine.

Cysteine means L- or D-cysteine, preferably L-cysteine.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are Copper(II) sulphate pentahydrate ($CuSO_4.5H_2O$), Sodium Chloride (NaCl), Calcium chloride ($CaCl_2.2H_2O$), Potassium chloride (KCl), Iron(II)sulphate, sodium phosphate monobasic anhydrous ($NaH_2PO_4$), Magnesium sulphate anhydrous ($MgSO_4$), sodium phosphate dibasic anhydrous ($Na_2HPO_4$), Magnesium chloride hexahydrate ($MgCl_2.6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, flavin mononucleotide and derivatives, glutathione, heme nucleotide phosphates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

Feed media may have a different composition compared to full media. They typically comprise amino acids, trace elements and vitamins. They might also comprise saccharide components but sometimes for production reasons the saccharide components are added in a separate feed.

A suitable feed medium to be used according to the method of the present invention might for example comprise in addition to S-sulfocysteine one or more of the following compounds, but no cysteine or cystine:
L-ASPARAGINE MONOHYDRATE
L-ISOLEUCINE
L-PHENYLALANINE
SODIUM L-GLUTAMATE MONOHYDRATE
L-LEUCINE
L-THREONINE
L-LYSINE MONOHYDROCHLORIDE
L-PROLINE
L-SERINE
L-ARGININE MONOHYDROCHLORIDE
L-HISTIDINE MONOHYDROCHLORIDE MONOHYDRATE
L-METHIONINE
L-VALINE
MONO-SODIUM-L-ASPARTATE-MONOHYDRATE
L-TRYPTOPHAN
CHOLINE CHLORIDE
MYO-INOSITOL
NICOTINAMIDE
CALCIUM-D(+) PANTOTHENATE
PYRIDOXINE HYDROCHLORIDE
THIAMINE CHLORIDE HYDROCHLORIDE
VITAMIN B12 (CYANOCOBALAMINE) MICRONIZED
BIOTIN
FOLIC ACID
RIBOFLAVIN
MAGNESIUM SULFATE ANHYDROUS
COPPER(II) SULFATE PENTAHYDRATE
ZINC SULFATE HEPTAHYDRATE
1,4-DIAMINOBUTANE DIHYDROCHLORIDE
AMMONIUM HEPTAMOLYBDATE TETRAHYDRATE
CADMIUM SULFATE HYDRATE
MANGANESE(II) CHLORIDE TETRAHYDRATE
NICKEL(II) CHLORIDE HEXAHYDRATE
SODIUM META SILICATE
SODIUM METAVANADATE
TIN(II) CHLORIDE DIHYDRATE
SODIUM SELENITE (ABOUT 45% SE)
SODIUM DIHYDROGEN PHOSPHATE MONOHYDRATE
AMMONIUM IRON(III) CITRATE (ABOUT 18% FE)

The gist of the present invention is to decrease the amount of trisulfide bonds found in the protein or, preferably, IgG which is produced in the cell culture by replacing cysteine and/or cystine by S-sulfocysteine and/or its salts.

It has been found that trisulfide linkage formation between the light chain and the heavy chain in said proteins, especially antibodies, is reduced efficiently, typically more than 75%, compared to cell culture without replacing cysteine and/or cystine in the feed by S-sulfocysteine and/or its salts.

Surprisingly, the reduction of another trisulfide formation was found. Trisulfide formation in said proteins, especially antibodies, in the linkage between cysteine 259 and cysteine 319 in the heavy chain was found and it could also be reduced with the method of the invention.

The cells to be treated with a feed medium comprising S-sulfocysteine and/or its salts instead of cysteine and/or cystine according to the invention are typically cells that are cultured in a bioreactor for biopharma production purposes.

S-sulfocysteine and/or its salts can be added to the cells at any stage of the cell culture, comparable to the addition of cysteine and/or cystine.

It can be added when starting the cell culture. In this case, S-sulfocysteine and/or its salts are preferably mixed and milled with the other ingredients of the base medium which is used to start the cell culture. This dry powder mixture comprising S-sulfocysteine and/or its salts is then dissolved in a suitable solvent by admixing the powder and the solvent such that the powder dissolves and produces a liquid cell culture medium with a desired and homogenous concentration of the media components.

S-sulfocysteine and/or its salts can also be added one or more times during the culturing of the cells. A cell culture is typically performed for 1 to 3 weeks. During this time feed medium is added either continuously or one or more times. S-sulfocysteine and/or its salts can be added to the culture in a feed medium together with other feed medium ingredients or it can be added in a separate feed which only comprises S-sulfocysteine and/or its salts. Also the feed is typically a liquid so that all components of the feed are dissolved in a suitable solvent prior to the addition to the cell culture.

In a preferred embodiment, the cell culture is started with a base medium comprising cysteine and/or cystine but no S-sulfocysteine and/or its salts and S-sulfocysteine and/or its salts are added as feed. It is preferably added at least 4 times during cell culture, preferably between 4 and 6 times. In one embodiment, S-sulfocysteine and/or its salts is added between every second and every fourth day.

The pH of the feed comprising S-sulfocysteine and/or its salts is typically between 5 and 7.5, preferably between 6.8 and 7.5, most preferred between 6.8 and 7.1.

Typically a Cell Culture is Performed By
a) providing a bioreactor
b) mixing the cells to be cultured with a liquid cell culture medium in the bioreactor
c) incubating the mixture of step b) for a certain time whereby a feed medium comprising S-sulfocysteine but no significant amounts of, preferably no, cystine or cysteine is added at least once during that time A bioreactor is any container, bag, vessel or tank in which cells can be cultured. Performing a cell culture is known to a person skilled in the art. This is typically done by incubating the cells in the bioreactor under suitable conditions like pH, osmolality, temperature, agitation, aeration (oxygen/$CO_2$) etc. and the optional addition of feed media one or several times during the cell culture. Preferably, the cell culture is performed as fed-batch cell culture.

Fed-batch culture is a cell culture process where one or more nutrients (substrates) are fed (supplied) to the bioreactor during cultivation of the cells and in which the product(s) remain in the bioreactor until the end of the run. An alternative description of the method is that of a culture in which a base medium supports the initial cell culture and a feed medium is added to prevent nutrient depletion. The advantage of the fed-batch culture is that one can control concentration of fed-substrate in the culture liquid at arbitrarily desired levels.

Generally speaking, fed-batch culture is superior to conventional batch culture when controlling concentrations of a nutrient (or nutrients) affect the homogeneity or yield of the desired metabolite, like in this case S-sulfocysteine and/or its salts.

Consequently, preferably, the present invention is performed by
Filling into a bioreactor cells and liquid cell culture medium
Incubating the cells in the bioreactor
Continuously over whole time of the incubation of the cells in the bioreactor or once or several times within said incubation time adding a cell culture medium, which is in this case a feed medium, to the bioreactor
whereby the feed medium comprises S-sulfocysteine and/or its salts but no significant amounts of, preferably no, cysteine and/or cystine and preferably has a pH between 6.8 and 7.5.

It has been found that the reduction of the amount of trisulfide bonds is especially effective if the cell culture comprises as less cysteine and/or cystine as possible. As a consequence, if the cells are able to be grown with S-sulfocysteine and/or its salts alone, preferably, the cell culture does not comprise any cysteine and/or cystine. For some cells the base medium needs to comprise cysteine and/or cystine as they do not show sufficient performance and/or growth in media which comprise S-sulfocysteine and/or its salts but do not contain any cysteine and/or cystine. In this case, preferably, the base medium comprises cysteine and/or cystine and the feed media that are added during culture do not comprise any additional cysteine and/or cystine.

It is obvious to a person skilled in the art that one or several types of feed media can be added to the cell culture. If a single feed strategy is used, only one type of feed media is added to the cell culture, either continuously, or one or several times during cell culture. According to the method of the invention, this single feed medium does not contain any significant amounts cysteine and/or cystine but S-sulfocysteine and/or its salts as a replacement. If several different feed media added to a cell culture, according to the method of the invention, preferably none of these feed media contains cysteine and/or cystine. It is not necessary that all feed media contain S-sulfocysteine and/or its salts. It might for example be favourable to add a feed comprising vitamins, trace elements and amino acids as well as S-sulfocysteine and/or its salts and a second feed at other times whereby the second feed is e.g. a carbohydrate feed which preferably does not comprise any S-sulfocysteine and/or its salts. In any case, at least once during cell culture a feed is added which does not contain any significant amounts or preferably no cysteine and/or cystine but which comprises S-sulfocysteine and/or its salts.

It has been found that with the method of the present invention, the amount of trisulfides can be reduced effectively. Preferably, trisulfide formation between the light chain and the heavy chain can be reduced. This trisulfide formation can be reduced by more than 75%, preferably more than 85% compared to cell culture processes in which cystine and/or cysteine in the feed medium are not replaced by S-sulfocysteine and/or its salts.

Proteins that have been treated according to the method of the present invention and for which trisulfide bond formation has been reduced can be used in diagnostic assays, immunoassays and/or pharmaceutical compositions.

In some embodiments, the protein, e.g. antibody, treated with the method of the present invention has increased storage stability compared to an untreated control. In another embodiment, the protein, e.g. antibody, treated with the method of the present invention has a decreased tendency to aggregate compared to an untreated control. In still another embodiments, treatment of a protein, e.g. antibody, with the method of the present invention results in decreased oxidation, e.g. methionine oxidation, as compared to an untreated control.

Therefore, the present invention also provides a method for reducing protein oxidation, e.g. methionine oxidation, in a composition of proteins, e.g. antibodies, comprising reducing the level of trisulfides in the composition of proteins. Another embodiment provides a method for reducing protein aggregation in a composition of proteins, e.g. antibodies, comprising reducing the level of trisulfides in the composition of proteins. Another embodiment provides a method of increasing protein stability in a composition of proteins, e.g. antibodies, comprising reducing the level of trisulfides in the composition of said proteins.

Another embodiment provides a method of increasing or enhancing long-term protein and antibody storage stability. by converting trisulfide bonds to disulfide bonds in an antibody by performing the process steps described above.

The present invention is further illustrated by the following figures and examples, however, without being restricted thereto.

The entire disclosure of all applications, patents, and publications cited above and below as well as the corresponding patent application EP 16167461.9 filed on Apr. 28, 2016 are hereby incorporated by reference.

EXAMPLES

The following examples represent practical applications of the invention.
1. Protocols
a. Fed-Batch Process Recombinant CHO cells expressing an IgG1 were grown in fully chemically defined basal media (Cellvento® CHO 220) containing 1.5 mM cysteine. At days 3, 5, 7, 10, 14; feed(s) containing either cysteine or S-sulfocysteine were added.

For the control condition, the main feed included vitamins, trace elements and amino acid except cysteine because of the low stability of this amino acid. 150 mM of cysteine was dissolved in a separate feed at pH 11. The main feed was added at 3%, 6%, 6%, 6% and 6% (v/v) whereas cysteine was added at 0.3%, 0.6%, 0.6%, 0.6% and 0.6% on day 3, 5, 7, 10 and 14, respectively.

For the SSC condition, the main feed included the same vitamins, trace elements and amino acids and was further supplemented with 15 mM of S-sulfocysteine di-sodium salt. The main feed was added 3%, 6%, 6%, 6% and 6% (v/v) day 3, 5, 7, 10 and 14 respectively, resulting in the same amount of cysteine source when compared to the control condition. Glucose was monitored on a daily basis for both conditions and adjusted to 6 g/L using a 400 g/L solution.

The process was performed in 1.2 L bioreactors at 37° C., pH 7.0, 50% dissolved oxygen, agitation 140 rpm.

Samples were taken from the bioreactors for the trisulfide analysis on day 13 and day 18. After sampling, cell culture supernatant was centrifuged 5 min at 1500 rpm, the IgG concentration was quantified using an automatic turbidometric method (Cedex bioHT) and frozen for further processing.

b. IgG Purification from the Cell Culture Supernatant

IgG were purified from the frozen samples using protein A binding (Phytips method) and were eluted in 200 mM NAH2PO4; 140 mM NaCl and 96 mM Tris HCl and quantified again.

c. Peptide generation from the IgG

First, the free cysteines in the samples were alkylated by addition of N-ethylmaleiimide (10 mM solution in 0.1 M Na acetate buffer pH 5.0) for 30 min in the dark.

For digestion with Lys-C, 55 μL digestion buffer (8 M urea, 0.1 M Tris, pH 7) and 15 μL Lys-C enzyme (Promega, V1671) were added and the samples were incubated for 4 hours at 37° C. Subsequently, the samples were diluted to 1 M urea by addition of 468 μl digestion buffer and were digested by addition of 12 μL trypsin over night at 37° C. The final antibody concentration was 50 mg/L. For the analysis of the disulfide and trisulfide bonds, the sample was treated with 10% formic acid (4.4 μL) to stop the digestion and analyzed by LC-MS.

d. LC-MS/MS Method

The peptide mixture obtained was injected and separated using reversed phase HPLC (RSLC3000 nano LC, Thermo Scientific Dionex, Idstein, Germany). A nanoLC column (Acquity UPLC M-Class HSS T3, 1.8 μm, 75 μm×150 mm, Waters) with a cartridge (PM100, C18, 5 μm, 0.3×5 mm, Thermo Scientific Dionex, Idstein, Germany) was used for preconcentration and separation of the sample. Blank runs and column wash runs were performed within consecutive sample runs.

An optimized 26-minute linear gradient with varying slopes was applied at 50° C. as follows (minute/% B): 0/2, 0.25/2, 8/16, 20/29, 26.25/45, 27.25/99, 30.25/99 31.25/20 32.25/20, 33.25/99, 34.25/99, 35.25/2, 38/2. The injection amount was 5-7 μL (~0.35 μg). The sample was loaded at a flow rate of 120 μL/min onto the cartridge for 0.25 minutes. For loading, an eluent composed of 97.95% water, 2% acetonitrile and 0.05% TFA was used. Subsequently, the valve switched, the sample was transferred to the analytical column and separated using a flow rate of 0.6 μL/min. The HPLC eluat was directly infused into a QExactive plus mass spectrometer (Thermo scientific, Bremen, Germany). The mass spectrometer operated in positive ion mode, the spray voltage was 1.9 kV, the capillary temperature was 275° C. and the S-Lens RF voltage was 55 V. For the MS/MS product ion scan, the activation type was collision-induced dissociation (CID), the default charge state was 2. The 4-scan-event QExactive method applied consists of a full MS survey scan at m/z 200-2000 and resolution power (RP) of 70 000 followed by three cycles of data-dependent MS/MS scans on the top three most intense ions. The dynamic exclusion function was enabled and parameters were as follows: dynamic exclusion of 10 sec, isolation window of 2 m/z, resolution of 17 500, AGC target 3e6, maximum inject time of 250 msec, normalized collision energy of 25, underfill ratio of 0.1%, intensity threshold of 1.2e4. Unassigned charge states and charge state 8 were rejected for MS/MS triggering and a reject mass list containing polysiloxane ions was enabled. Dynamic exclusion was 10 s. Replicate runs were performed with and without charge state +1 exclusion. For data processing the Mascot 2.3 error tolerant search (Matrix Science London, UK) based on an in house protein database that contained the sequences of the light and heavy chain of the analyzed antibody respectively, was used. MS/MS spectra were charge deconvoluted using MS2 processor before database search and Mascot settings were adapted to allow identification of small peptides: the shortest peptide tested in the search and evidenced in the report was set to 4 amino acids. Mascot search parameters were: enzyme was trypsin, 2 missed cleavages allowed, fixed modification carbamidomethylation for the tryptic digest, peptide tolerance: 6 ppm, MS/MS tolerance 0.05 Da, peptide charge +2, +3, +4, error tolerant search activated, minimum ion score 15.

2. Results

FIGS. 2-5 show the results of the quantification of the trisulfide formation between the light chain and the heavy chain of the IgG (LC-HC) as well as the between 2 cysteine residue of the HC (HC_cys259-Cys319) on day 13 and 18 respectively.

The relative percentage of trisulfide linked peptide was calculated by dividing the area of the trisulfide linked peptide by the sum of the areas of the trisulfide and disulfide linked peptide.

Results indicate that the highest amount of trisulfide was found for the LC-HC linked peptides in the control samples produced using cysteine in the separate feed. The amount of trisulfide decreases in the samples produced using SSC feed. The mean reduction of trisulfide is of 93.3% at day 13 and 92.4% at day 18 when using SSC when compared to the control condition. Three orders of magnitude lower, we found evidence for trisulfide formation in the linkage between cysteine 259 and cysteine 319 in the heavy chain. Although the relative amount is very low, the data are highly consistent and confirm the trend observed for the trisulfide formation between the LC-HC linkage. The amount of trisulfide decreases in the samples produced using SSC feed. The mean reduction of trisulfide is of 46.7% at day 13 and 25.9% at day 18 when using SSC when compared to the control condition.

Figure 6:
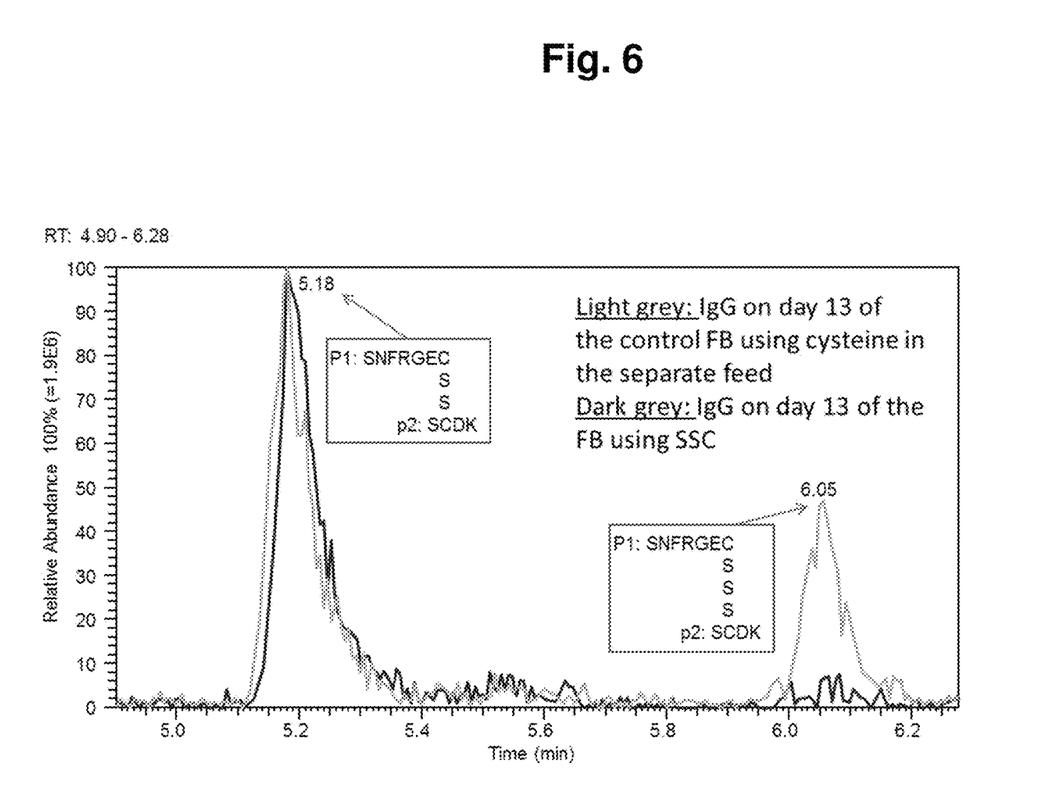
FIG. 6 shows the overlay of extracted ion chromatograms showing the relation between the LC-HC link with a disulfide bridge and the LC-HC link with a trisulfide bridge. Further details can be found in the examples.

FIG. 6 shows the overlay of extracted ion chromatograms showing the relation between the LC-HC link with a disulfide bridge and the LC-HC link with a trisulfide bridge.

FIG. 6 illustrates the relative decrease of the trisulfide formation in the LC-HC linkage in the FB using SSC (dark grey) with respect to the disulfide linked peptide when compare to the LC-HC linkage in the control FB using cysteine in the separate feed (light grey).

The invention claimed is:

1. A method for reducing the formation of trisulfide bonds in proteins comprising:
culturing cells expressing said proteins in a cell culture, wherein during the cell culturing a feed medium is added to the cell culture one or more times and said feed medium does not contain significant amounts of cysteine or cystine but comprises S-sulfocysteine and/or salts thereof,
wherein said proteins exhibit trisulfide bonds when expressed by cells cultured in a cell culture medium using a feed medium in which cysteine and/or cystine is not replaced by S-sulfocysteine and/or salts thereof,
detecting reduced trisulfide linkage formation in said proteins in cells cultured in said feed medium comprising S-sulfocysteine and/or salts thereof relative to protein expressed by cells cultured in a cell culture medium where cysteine and/or cysteine in the feed medium has not been replaced by S-sulfocysteine and/or salts thereof.

2. The method according to claim 1, wherein the S-sulfocysteine and/or salts thereof is S-sulfocysteine sodium salt.

3. The method according to claim 1, wherein S-sulfocysteine and/or a S-sulfocysteine salt are added in the feed medium in an amount so that their concentration in the cell culture is between 0.4 and 50 mM.

4. The method according to claim 1, wherein the cells are cultured in a cell culture medium comprising at least one or more saccharide components, one or more amino acids, one or more vitamins or vitamin precursors, one or more salts, one or more buffer components, one or more co-factors and one or more nucleic acid components.

5. The method according to claim 1, wherein the pH of the feed medium comprising S-sulfocysteine and/or salts thereof is between 6.8 and 7.5.

6. The method according to claim 1, wherein the feed medium further comprises vitamins, trace elements and amino acids.

7. The method according to claim 1, wherein said proteins exhibit a light chain and a heavy chain and trisulfide linkage formation between the light chain and the heavy chain in said proteins is reduced.

8. The method according to claim 1, wherein said proteins exhibit a heavy chain containing cysteine 259 and cysteine 319, and trisulfide formation in the linkage between cysteine 259 and cysteine 319 in the heavy chain in said proteins is reduced.

9. The method according to claim 1, wherein the method is performed by
Filling the cells and a liquid cell culture medium into a bioreactor,
Incubating the cells in the bioreactor, and
Continuously over the whole time of the incubation of the cells in the bioreactor, or once or several times during said incubation, adding said feed medium to the bioreactor.

10. The method according to claim 1, wherein the feed medium comprises S-sulfocysteine and/or a S-sulfocysteine salt in a concentration between 1 and 100 mmol/l.

11. The method according to claim 9, wherein over the whole time of the incubation of the cells in the bioreactor no feed medium is added which contains cysteine and/or cystine.

12. The method according to claim 1, wherein over the whole time of the culturing of the cells no feed medium is added which contains cysteine and/or cystine.

13. The method according to claim 1, wherein the feed medium comprises S-sulfocysteine and/or a S-sulfocysteine salt in a concentration between 5 and 20 mmol/l.

14. The method according to claim 1, wherein the feed medium comprises S-sulfocysteine and/or a Li, Na, L, Ca, or Mg salt thereof.

15. The method according to claim 1, wherein the feed medium contains cysteine and/or cystine in an amount of less than 5% (w/w) of the amount of S-sulfocysteine and/or its salts.

16. The method according to claim 1, wherein the cells expressing said protein are CHO cells, COS cells, I VERO cells, BHK cells, AK-1 cells, SP2/0 cells, L5.1 cells, hybridoma cells or human cells.

17. The method according to claim 1, wherein the cells expressing said protein are CHO-S, CHO dhfr- (DG44 and Duxb11), CHO-M, or CHOK1 cells.

18. The method according to claim 1, wherein said protein is an antibody.

19. The method according to claim 18, wherein said antibody is an IgG.

20. The method according to claim 1, wherein the cell culture is started with a base medium comprising cysteine and/or cystine but no S-sulfocysteine and/or its salts before the feed medium is added.

* * * * *